United States Patent [19]
Sistig et al.

[11] Patent Number: 5,264,094
[45] Date of Patent: Nov. 23, 1993

[54] PROCESS FOR THE PREPARATION OF FLUOROBENZENES

[75] Inventors: Frank P. Sistig, Hofheim am Taunus; Ernst I. Leupold, Neu-Anspach; Heinz Litterer, Bad Schwalbach, all of Fed. Rep. of Germany

[73] Assignee: Hoechst Aktiengesellschaft, Frankfurt am Main, Fed. Rep. of Germany

[21] Appl. No.: 849,059

[22] PCT Filed: Oct. 18, 1990

[86] PCT No.: PCT/EP90/01762
§ 371 Date: Apr. 24, 1992
§ 102(e) Date: Apr. 24, 1992

[87] PCT Pub. No.: WO91/06518
PCT Pub. Date: May 16, 1991

[30] Foreign Application Priority Data

Oct. 27, 1989 [DE] Fed. Rep. of Germany ....... 3935862

[51] Int. Cl.$^5$ .............. C07C 17/33; C07C 25/13; C07G 13/00
[52] U.S. Cl. .............. 204/157.97; 570/142
[58] Field of Search .............. 570/142; 204/157.97

[56] References Cited

U.S. PATENT DOCUMENTS 4,847,442 7/1989 Nalewajek et al. ............ 570/142
4,937,395 6/1990 Litterer et al. ............ 570/142
4,968,852 11/1990 Kawai et al. ............ 570/142

FOREIGN PATENT DOCUMENTS 3824141 1/1990 Fed. Rep. of Germany .

OTHER PUBLICATIONS

Collection Czechoslov. Chem. Commun. 37, 3042–3051 (1972).

Primary Examiner—Joseph E. Evans
Attorney, Agent, or Firm—Connolly and Hutz

[57] ABSTRACT

Process for the preparation of fluorobenzenes having at least one hydrogen atom as ring substituent and, optionally, further substituents, which, independently of each other, can be chlorine, bromine, nitro, hydroxyl, $C_1$–$C_3$-alkoxy or $C_1$–$C_3$-alkyl, the number of nitro groups being not more than 2 and the number of hydroxyl groups and alkoxy groups being not more than 3 in each case, by heating the corresponding benzaldehydes, substituted by at least one flourine atom, in the presence of a catalyst, characterized in that the reaction product is immediately removed from the reaction zone.

9 Claims, No Drawings

PROCESS FOR THE PREPARATION OF FLUOROBENZENES

DESCRIPTION

The present invention relates to a process for the preparation of optionally substituted fluorobenzenes by thermal decarbonylation of the corresponding benzaldehydes with the aid of transition metal catalysts. Many of the substituted fluorobenzenes are valuable intermediates in the preparation of compounds having herbicidal, fungicidal or insecticidal activity; they are likewise usable for the preparation of important pharmaceutical active substances.

Fluorobenzenes have hitherto been prepared from the corresponding substituted anilines by diazotization and subsequent replacement of the diazo group by fluorine. Thus the preparation of fluorobenzene by diazotization of aniline hydrochloride, conversion of the resulting benzenediazonium chloride into the tetrafluoroborate and subsequent heating has long been known (G. Balz and G. Schiemann, Ber. 60 (1927) 1188; D. T. Flood, Org. Synth. Coll. Vol II (1943) 295). In addition, the preparation of fluorobenzene by diazotization of aniline in anhydrous hydrogen fluoride at 0° C. with subsequent decomposition of the resulting benzenediazonium fluoride at 20° C. is also described (Kirk-Othmer, Encyclopedia of Chemical Technology, 3rd ed. Vol. 10, p. 908). 1,3-Difluorobenzene could be obtained analogously in a 31% yield, relative to m-phenylenediamine as starting compound, by heating benzene-1,3-bis-diazonium tetrafluoroborate (G. Schiemann and R. Pillarsky, Ber. 62 (1929) 3035–3043, especially 3029). The diazotization of 3-fluoroaniline in anhydrous hydrogen fluoride in the presence of either ammonium fluoride or tertiary amines or dimethyl sulfoxide produced in each case 1,3-difluorobenzene in a yield of 46 to 73% (U.S. Pat. No. 4,075,252 and U.S. Pat. No. 4,096,196).

The decarbonylation of aromatic aldehydes with replacement of the formyl group by hydrogen is a reaction which is described many times in the literature. The reaction is catalyzed inter alia by transition metal such as chromium, manganese, nickel, copper or zinc, but in particular by metals of the platinum group. For reasons of cost, these metals are generally precipitated on inert support materials. However, the use of soluble noble metal complexes is also described, whereby it is possible to carry out the reaction in homogeneous solution (Houben-Weyl, Methoden der Organischen Chemie [Methods in Organic Chemistry], Volume V/2b (1981) 332–336, Georg Thieme Verlag, Stuttgart).

The decarbonylation of fluorine-substituted benzaldehydes has only hitherto been achieved, however, in an economically untenably low yield. Thus, 1,3-difluorobenzene was obtained by heating 2,6-difluorobenzaldehyde in 50% strength aqueous potassium hydroxide solution in a yield of about 70% (G. Lock, Ber. 69 (1936) 2253).

Using the Balz-Schiemann process, unsubstituted or substituted fluorobenzenes can frequently only be obtained in unsatisfactory yield. It is, moreover, generally associated with the processing disadvantage that large amounts of salt are produced. The object was therefore to develop a process by which fluorobenzenes, which can be still further substituted, can be obtained in high yields from the corresponding fluorobenzaldehydes.

It has now been found that fluorobenzenes can be obtained in high yields by thermal decarbonylation from fluorine-substituted benzaldehydes if the resulting fluorobenzenes are immediately removed from the reaction zone. Since the fluorobenzenes have a lower boiling point than the fluorobenzaldehydes, this takes place in a particularly simple manner, by employing conditions under which the desired fluorobenzene is volatile and can be removed.

The invention thus relates to a process for the preparation of fluorobenzenes having at least one hydrogen atom as ring substituent and, optionally, further substituents, which, independently of each other, can be chlorine, bromine, nitro, hydroxyl, $C_1$–$C_3$-alkoxy or $C_1$–$C_3$-alkyl, the number of nitro groups being not more than 2 and the number of hydroxyl groups and alkoxy groups being not more than 3 in each case, by heating the corresponding benzaldehyde, substituted by at least one fluorine atom, in the presence of a catalyst, characterized in that the reaction product is immediately removed from the reaction zone. It is expedient if the number of nitro groups and hydroxyl groups is not more than 2 in each case and the number of hydroxyl groups and alkoxy groups together is not more than 3.

Suitable starting materials for the process according to the invention are benzaldehydes which are substituted by one or more fluorine atoms; at least one other substituent can additionally be present, for example chlorine, bromine, nitro, hydroxyl, $C_1$–$C_3$-alkoxy and/or $C_1$–$C_3$-alkyl.

Suitable catalysts for the process according to the invention expediently contain one or more transition metals from subgroup I, II, VI, VII and VIII, such as chromium, manganese, nickel, copper or zinc, but preferably one or more metals selected from the platinum metals group, in particular rhodium. In this case, the process can be carried out in a heterogeneous system using solid catalysts on supports or in a homogeneous system in the liquid phase.

Soluble rhodium complexes, which can be employed in a homogeneous liquid system or with which supports can be impregnated are for example rhodium(I) complexes such as $ClRh(PPh_3)_3$ ("Wilkinson catalyst"), $ClRh(CO)(PPh_3)_2$, $[ClRh(CO)_2]_2$, $acacRh(CO)(PPh_3)$, $acacRh(CO)_2$, $(C_5H_5)Rh(C_8H_{14})$ and $(C_3H_5)Rh(PPh_3)_2$, where Ph is phenyl, acac is acetylacetonate, $C_8H_{14}$ is cyclooctene, $C_5H_5$ is cyclopentadienyl $C_3H_5$ is allyl. Suitable complexes are also rhodium(II) complexes and rhodium(III) complexes such as rhodium(II) acetate, rhodium(II) 2,4-difluorobenzoate, $Rh(acac)_:$, $RhCl_3.xH_2O$, $Rh(NO_3)_3$ and $(C_3H_5)RhCl_2(PPh_3)_2$. Further compounds which can act as ligands, such as phosphines, phosphites or amines, can advantageously be added to these rhodium complexes.

The process according to the invention can be carried out in all apparatuses suitable for liquid phase reactions. A solution which is simple in terms of apparatus is a stirred vessel having a distillation column mounted on it. If a heterogeneous system is employed, the catalyst can be present in suspension or arranged in solid form.

Pressure and temperature are advantageously selected in the homogeneously and in the heterogeneously catalyzed decarbonylation process such that as complete as possible an elimination of the desired reaction products from the reaction mixture is ensured. Expediently, a temperature of 120° to 300° C. is employed, preferably 150° to 200° C. Depending on the type of reaction product desired, a pressure of 0.01 to 10 bar can be employed. The pressure is preferably in the range from 0.1 to 3 bar, particularly preferably in the range from 1.0 to 1.2 bar.

The starting material can be introduced all at once, or, preferably, continuously fed to the reaction zone. A combination is also possible, that is introduction of a portion and subsequent metering in of the remaining portion. When starting materials are used which gradually deactivate the catalyst, it has proved to be advantageous to remove small quantities of the reaction mixture continuously or discontinuously and to replace the quantity of catalyst removed by an equivalent amount of fresh catalyst.

According to a particular embodiment of the process according to the invention, the reaction mixture is subjected to the action of microwaves, whereby a still higher yield can be achieved.

The following comparison examples V1 and V2 show that the CO partial pressure (V1 1 bar, V2 25 bar) has virtually no influence on the decarbonylation reaction. In both experiments approximately 12% of 1,3-difluorobenzene was obtained after a reaction time of 72 h. This is notable insofar as an increase in the CO partial pressure near the reaction equilibrium should lead to a reduction of the yield. The decarbonylation therefore does not proceed near the equilibrium, and the resulting reaction products CO and the optionally substituted fluorobenzene do not produce a signficant shift in equilibrium. Therefore it is all the more surprising and unexpected that the immediate elimination of the products from the reaction mixture leads to high conversions and yields.

COMPARISON EXAMPLES

V1. 258 g of 2,4-difluorobenzaldehyde and 3.3 g of ClRh(PPh$_3$)$_3$ were stirred in a 500-ml flask equipped with reflux condenser at 170° C. under a CO pressure of one atmosphere. After 72 h the mixture was cooled. The reaction mixture contained 31 g of 1,3-difluorobenzene (12.5% by weight).

V2. 256 g of 2,4-difluorobenzaldehyde and 3.3 g of ClRh(PPh$_3$)$_3$ were stirred in a 10-l stainless steel autoclave under a CO pressure of 22 bar at 170° C. The pressure was slowly increased to 28 bar. After 72 h the mixture was cooled and the reaction mixture was analyzed. It contained 12.4% by weight of 1,3-difluorobenzene (30.8 g).

EXAMPLES

1. A rhodium catalyst comprising 74 mmol of Rh—prepared from 20 g of RhCl$_3$.xH$_2$O (38% Rh content), 50 g of triphenylphosphine, 15 g of water and 32 g of 2,4-difluorobenzaldehyde—in 9645 g of 2,4-difluorobenzaldehyde was introduced into a 10-l flask equipped with a distillation attachment, composed of a 50-cm long Vigreux column, a dephlegmator (operated at 86° C.) and a distillation head. After heating to about 170° C. and an induction time of approximately 20 h, 21 g of 1,3-difluorobenzene were formed per hour. As the liquid level fell, the activity of the catalyst decreased and after 40 days no more product was produced. The combined fractions of 7360 g having contents of greater than 99% of 1,3-difluorobenzene corresponded to a yield of 95%.

2. A rhodium catalyst comprising 40 mmol of rhodium was introduced together with 1500 g of 2,4-difluorobenzaldehyde into a 2-l flask equipped with automatic compensation of the liquid level at the bottom and the distillation attachment described in Example 1, and the mixture was heated to 168°-175° C. 20 to 25 g of 1,3-difluorobenzene were produced per hour in the receiver, unreacted 2,4-difluorobenzaldehyde having been continuously replaced in the apparatus. After an operating time of 1000 h, 19.62 kg of 1,3-difluorobenzene had been obtained. Analysis of the bottom product gave a residue of 3% by weight, relative to the amount used.

After 1000 hours of operation, 20% of the bottom product was withdrawn and the amount of catalyst contained therein was replaced by an equivalent amount of fresh catalyst, to allow continuous operation.

3. 5.14 g of RhCl$_3$.xH$_2$O (as in Example 1), 15.7 g of triphenylphosphine and 495 g of 2,4-difluorobenzaldehyde were introduced into a modified apparatus having a 1-l reaction flask, a further 500 g of 2,4-difluorobenzaldehyde were added and the flask was then irradiated with microwaves at a frequency of 2450 MHz and a power of approximately 350 W. After an induction time of approximately 20 hours, 278 g of 1,3-difluorobenzene (content greater than 99%) were obtained per day. 2,4-Difluorobenzaldehyde was continuously replenished, so that the filling level in the reaction flask remained virtually constant. In the course of 100 h, no decrease in the activity of the catalyst was detectable.

4. 40 g of 2-chloro-6-fluorobenzaldehyde and a rhodium catalyst prepared according to Example 1 and containing 1 mmol of rhodium were stirred at 200° C. in a 500-ml flask equipped with a distillation attachment. After 400 h, no more product was produced, that is the reaction was completed (yield 96%).

5. As described in Example 4, 42 g of 2-fluoro-5-nitrobenzaldehyde were reacted at 215° C. The reaction was completed after 200 h (yield 84%).

We claim:

1. Process for the preparation of fluorobenzene having at least one hydrogen atom as ring substituent and, optionally, further substituents, which, independently of each other, can be chlorine, bromine, nitro, hydroxyl, C$_1$-C$_3$-alkoxy or C$_1$-C$_3$-alkyl, the number of nitro groups being not more than 2 and the number of hydroxyl groups and alkoxy groups being not more than 3 in each case, wherein the corresponding benzaldehydes, substituted by at least one fluorine atom, are heated by microwaves in the presence of a catalyst, and the reaction product is immediately removed from the reaction zone.

2. Process for the preparation of fluorobenzene having at least one hydrogen atom as ring substituent and, optionally, further substituents which, independently of each other, can be chlorine, bromine, nitro, hydroxyl, C$_1$-C$_3$-alkoxy or C$_1$-C$_3$-alkyl, the number of nitro groups being not more than 2 and the number of hydroxyl groups and alkoxy groups being not more than 3 in each case, said process comprising:

heating the corresponding benzaldehyde, substituted by at least one fluorine atom, in a reaction zone in the presence of a rhodium catalyst, and immediately removing the resulting reaction product from the reaction zone, in which zone said corresponding benzaldehyde is present as a liquid.

3. Process according to claim 2, wherein the catalyst is employed in a homogeneous liquid phase which includes said benzaldehyde.

4. Process according to claim 2, wherein said process is carried out at 120° to 300° C.

5. Process according to claim 2, wherein said process is carried out at 150° to 200° C.

6. Process according to claim 2, wherein the reaction zone is under conditions which cause said reaction product to be volatile.

7. Process according to claim 2, wherein said corresponding benzaldehyde is 2,4-difluorobenzaldehyde.

8. Process for the preparation of fluorobenzene having at least one hydrogen atom as a ring substituent and, optionally, further substituents, which, independently of each other, can be chlorine, bromine, nitro, hydroxyl, $C_1$–$C_3$-alkoxy groups or $C_1$–$C_3$-alkyl, the number of nitro groups being not more than 2 and the number of hydroxyl groups and alkoxy groups being not more than 3 in each case, comprising:

heating a corresponding benzaldehyde, substituted by at least one fluorine atom, in a reaction zone in the presence of a rhodium catalyst, and immediately removing the reaction product from the reaction zone, in which zone said benzaldehyde is present as a liquid.

9. Process for the preparation of a fluorobenzene having at least one hydrogen atom as ring substituent and, optionally, further substituents which, independently of each other, can be chlorine, bromine, nitro, hydroxyl, $C_1$–$C_3$-alkoxy or $C_1$–$C_3$-alkyl, the number of nitro groups being not more than 3 in each case, said process comprising:

heating by energy in the form of microwaves, the corresponding benzaldehyde, substituted by at least one fluorine atom, in a reaction zone in the presence of a rhodium catalyst, and immediately removing the resulting reaction product from the reaction zone, in which zone said corresponding benzaldehyde is present as a liquid.

* * * * *